US00PP32693P3

(12) United States Plant Patent
Psenner

(10) Patent No.: US PP32,693 P3
(45) Date of Patent: Dec. 22, 2020

(54) ***PORTULACA* PLANT NAMED 'POR16000'**

(50) Latin Name: *Portulaca oleracea*
Varietal Denomination: POR16000

(71) Applicant: Thomas Psenner, Bozen (IT)

(72) Inventor: Thomas Psenner, Bozen (IT)

( * ) Notice: Subject to any disclaimer, the term of this patent is extended or adjusted under 35 U.S.C. 154(b) by 0 days.

(21) Appl. No.: 16/873,550

(22) Filed: Apr. 30, 2020

(65) Prior Publication Data

US 2020/0367415 P1 Nov. 19, 2020

(30) Foreign Application Priority Data

May 17, 2019 (CA) ..... PBR 19-9899

(51) Int. Cl.
*A01H 5/02* (2018.01)
*A01H 6/00* (2018.01)

(52) U.S. Cl.
USPC ..... Plt./471
CPC ..... *A01H 6/00* (2018.05)

(58) Field of Classification Search
USPC ..... Plt./471
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Portulaca* plant named 'POR16000', characterized by its compact, upright to outwardly spreading to eventually prostrate plant habit; vigorous growth habit and rapid growth rate; freely branching habit; early and freely flowering habit; long flowering period; large dark red-colored flowers; and good garden performance.

1 Drawing Sheet

Botanical designation: *Portulaca oleracea.*
Cultivar denomination: 'POR16000'.

CROSS-REFERENCE TO A RELATED APPLICATION AND STATEMENT REGARDING PRIOR DISCLOSURES BY INVENTOR/APPLICANT

This application claims priority to a Canadian Plant Breeders' Rights application filed on May 17, 2019, application number 19-9899. There have been no offers for sale anywhere in the world prior to the effective filing date of this Application and no accessibility to one of ordinary skill in the art could have been derived from the printed Plant Breeder's Rights documents.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Portulaca* plant, botanically known as *Portulaca oleracea* and hereinafter referred to by the name 'POR16000'.

The new *Portulaca* plant is a product of a planned breeding program conducted by the Inventor in Bozen, Italy. The objective of the breeding program is to create new heat-tolerant *Portulaca* plants with relatively short internodes and numerous attractive flowers.

The new *Portulaca* plant originated from a cross-pollination made by the Inventor in Bozen, Italy in May, 2015 of a proprietary selection of *Portulaca oleracea* identified as code number POR12005, not patented, as the female, or seed, parent with a proprietary selection of *Portulaca oleracea* identified as code number POR13109, not patented, as the male, or pollen, parent. The new *Portulaca* plant was discovered and selected by the Inventor as a flowering plant from within the progeny of the stated cross-pollination in a controlled greenhouse environment in Bozen, Italy in June, 2016.

Asexual reproduction of the new *Portulaca* plant by vegetative terminal cuttings in a controlled greenhouse environment in Bozen, Italy since September, 2016, has shown that the unique features of this new *Portulaca* plant are stable and reproduced true to type in successive generations.

SUMMARY OF THE INVENTION

Plants of the new *Portulaca* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'POR16000'. These characteristics in combination distinguish 'POR16000' as a new and distinct *Portulaca* plant:

1. Compact, upright to outwardly spreading to eventually prostrate plant habit.
2. Vigorous growth habit and rapid growth rate.
3. Freely branching habit.
4. Early and freely flowering habit.
5. Long flowering period.
6. Large dark red-colored flowers.
7. Good garden performance.

Plants of the new *Portulaca* can be compared to plants of the female parent selection. Plants of the new *Portulaca* differ primarily from plants of the female parent selection in the following characteristics:

1. Plants of the new *Portulaca* have shorter internodes than plants of the female parent selection.
2. Plants of the new *Portulaca* flower earlier than plants of the female parent selection.
3. Plants of the new *Portulaca* have larger flowers than plants of the female parent selection.

Plants of the new *Portulaca* can be compared to plants of the male parent selection. Plants of the new *Portulaca* differ primarily from plants of the male parent selection in the following characteristics:

1. Plants of the new *Portulaca* are more vigorous than plants of the male parent selection.
2. Plants of the new *Portulaca* have dark red-colored flowers whereas plants of the male parent selection have yellow-colored flowers.

Plants of the new *Portulaca* can be compared to plants of the *Portulaca oleracea* 'Pazzaz Deep Pink', not patented. In side-by-side comparisons, plants of the new *Portulaca* differ primarily from plants of 'Pazzaz Deep Pink' in the following characteristics:

1. Plants of the new *Portulaca* have larger flowers than plants of 'Pazzaz Deep Pink'.
2. Plants of the new *Portulaca* have dark red-colored flowers whereas plants of 'Pazzaz Deep Pink' have pink-colored flowers.

BRIEF DESCRIPTION OF THE PHOTOGRAPHS

The accompanying colored photographs illustrate the overall appearance of the new *Portulaca* plant showing the colors as true as it is reasonably possible to obtain in colored reproductions of this type. Colors in the photographs may differ slightly from the color values cited in the detailed botanical description which accurately describe the colors of the new *Portulaca* plant.

At the top of the photographic sheet (FIG. 1) is a side perspective view of a typical flowering plant of 'POR16000' grown in a container and at the bottom of the photographic sheet is a close-up view of a typical flowering plant of 'POR16000'.

DETAILED BOTANICAL DESCRIPTION

The aforementioned photographs and following observations and measurements describe plants grown during the spring in 15.25-cm containers in a polyethylene-covered greenhouse in St. Thomas, Ontario, Canada and under cultural practices typical of commercial *Portulaca* production. During the production of the plants, day temperatures averaged 33° C. and night temperatures averaged 15° C. Plants were pinched three weeks after planting and were twelve weeks from planting rooted cuttings when the photographs and description were taken. In the following description, color references are made to The Royal Horticultural Society Colour Chart, 2007 Edition, except where general terms of ordinary dictionary significance are used.

Botanical classification: *Portulaca oleracea* 'POR16000'.

Parentage:

*Female, or seed, parent*.—Proprietary selection of *Portulaca oleracea* identified as code number POR12005, not patented.

*Male or pollen parent*.—Proprietary selection of *Portulaca oleracea* identified as code number POR13109, not patented.

Propagation:

*Type*.—By vegetative terminal cuttings.

*Time to initiate roots, summer*.—About eight days at temperatures about 18° C. to 22° C.

*Time to initiate roots, winter*.—About twelve days at temperatures about 18° C. to 22° C.

*Time to produce a rooted young plant, summer*.—About three weeks at temperatures about 18° C. to 22° C.

*Time to produce a rooted young plant, winter*.—About four weeks at temperatures about 18° C. to 22° C.

*Root description*.—Fine, fleshy; typically white in color, actual color of the roots is dependent on substrate composition, water quality, fertilizers, substrate temperature and age of roots.

*Rooting habit*.—Moderately freely branching; dense.

Plant description:

*Plant and growth habit*.—Compact, upright to outwardly spreading to eventually prostrate plant habit; vigorous growth habit and rapid growth rate.

*Branching habit*.—Freely branching habit about five primary lateral branches each with about eleven secondary lateral branches developing per plant; pinching enhances branching potential.

*Plant height*.—About 14.5 cm.

*Plant diameter* (*area of spread*).—About 51.8 cm.

Lateral branch/peduncle description:

*Length*.—About 22.4 cm.

*Diameter*.—About 3.5 mm.

*Internode length*.—Relatively short, about 1.9 cm.

*Strength*.—Moderately strong, flexible.

*Texture and luster*.—Smooth, glabrous; moderately glossy.

*Color, developing*.—Close to 147D.

*Color, developed*.—Close to 146D; on abaxial surface, tinged with close to 182D.

Leaf description:

*Arrangement*.—Alternate, simple.

*Length*.—About 2.5 cm.

*Width*.—About 1.3 cm.

*Shape*.—Obovate.

*Apex*.—Cuspidate.

*Base*.—Cuneate.

*Margin*.—Entire.

*Texture and luster, upper and lower surfaces*.—Smooth, glabrous; fleshy, succulent; moderately glossy.

*Venation pattern*.—Pinnate.

*Color*.—Developing leaves, upper surface: Close to 137D. Developing leaves, lower surface: Close to 138C. Fully expanded leaves, upper surface: Close to 137B; along the margins, close to N186C; venation, close to 147D. Fully expanded leaves, lower surface: Close to 138C; venation, close to 138B.

*Petioles*.—Length: About 1.5 mm. Diameter: About 2 mm. Texture and luster, upper and lower surfaces: Smooth, glabrous; semi-glossy. Strength: Moderately strong. Color, upper surface: Close to 147D. Color, lower surface: Close to 144A.

Flower description:

*Flower arrangement*.—Single rotate flowers; freely flowering habit with 225 flowers developing per plant; flowers face mostly upright to outwardly.

*Fragrance*.—None detected.

*Natural flowering season*.—Plants begin flowering about six weeks after planting; in the garden, plants flower continuously from spring until autumn in Southern Ontario, Canada.

*Flower longevity*.—Flowers last about one day on the plant; flowers not persistent.

*Flower buds*.—Length: About 1.1 cm. Diameter: About 6 mm. Shape: Ovoid. Texture and luster: Smooth, glabrous; moderately glossy. Color: Close to 145A tinged with close to N77B.

*Flower diameter*.—About 3.8 cm.

*Flower length* (*height*).—About 2.1 cm.

*Petals*.—Quantity per flower: Corolla consists of five petals fused at the base. Length: About 2.3 cm. Width: About 2.1 cm. Shape: Obcordate. Apex: Emarginate. Base: Fused, truncate. Margin: Entire, slightly to moderately undulate. Texture and luster, upper surface: Smooth, glabrous, satiny; glossy. Texture and luster, lower surface: Smooth, glabrous; moderately glossy. Color: When opening, upper surface: Close to 53C with a sheen of close to N66A; at the base, close to 7A. When opening, lower surface: Close to 58B; at the base, close to 7B. Fully opened, upper surface: Close to 53C; towards the margins, close to 50A; at the base, close to 7A; venation, similar to lamina colors; main color becoming closer to N57A with development. Fully opened, lower surface: Close to 58B; towards the margins, close to 52A; at the base, close to 4B; venation, similar to lamina colors; with development, color becoming closer to 53D and N57B and at the base, close to 7B.

*Sepals*.—Quantity per flower: Two fused into a tubular calyx. Length: About 6 mm. Width: About 7 mm. Shape: Ovate. Apex: Acute. Base: Fused, acute. Margin: Entire. Texture and luster, upper and lower surfaces: Smooth, glabrous; slightly glossy. Color, upper surface: Close to 194C tinged with close to N77C to N77D. Color, lower surface: Close to 197C.

*Reproductive organs*.—Androecium: Quantity of stamens per flower: About 78. Filament length: About 4 mm. Filament color: Close to 9A tinged with close to 180C. Anther shape: Oblong. Anther length: Less than 1 mm. Anther color: Close to 21B. Amount of pollen: Abundant. Pollen color: Close to N25A. Gynoecium: Pistil length: About 1.1 cm. Style length: About 7 mm. Style color: Close to 180B. Stigma diameter: About 9 mm. Stigma color: Close to 23A and at the center, close to 180B. Ovary color: Close to 145A. Fruits and seeds: To date, fruit and seed development have not been observed on plants of the new *Portulaca*.

Garden performance: Plants of the new *Portulaca* have been observed to have good garden performance and to tolerate temperatures ranging from about 2° C. to about 40° C. and to be suitable for USDA Hardiness Zone 11.

Pathogen & pest resistance: To date, plants of the new *Portulaca* have not been shown to be resistant to pathogens and pests common to *Portulaca* plants.

It is claimed:

1. A new and distinct *Portulaca* plant named 'POR16000' as illustrated and described.

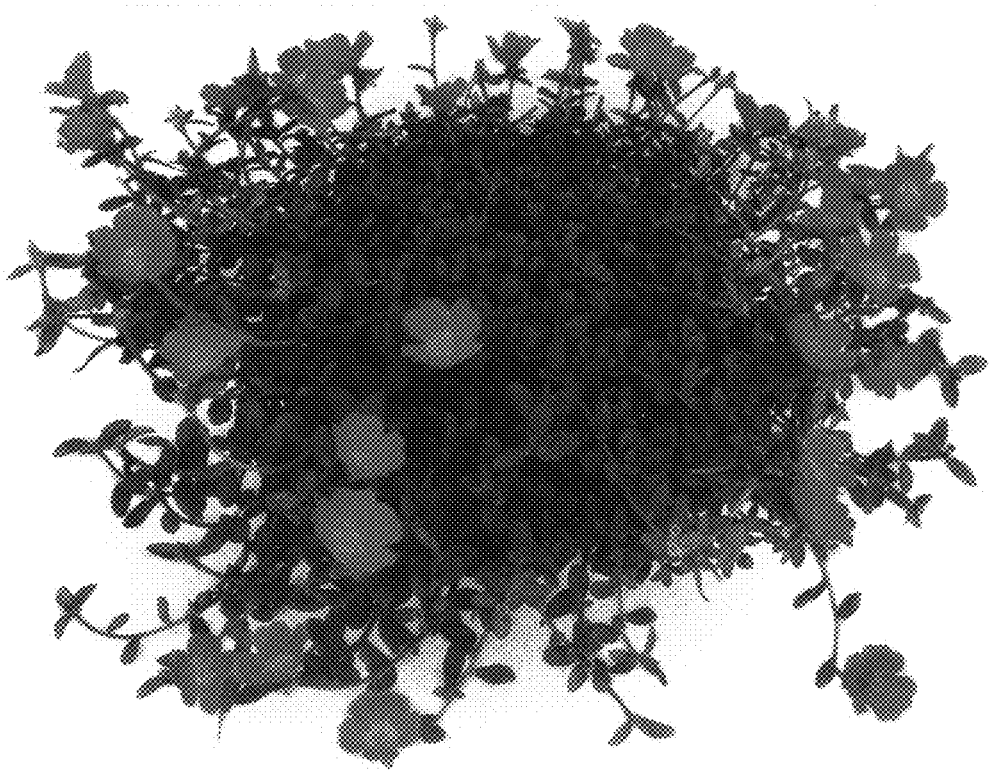
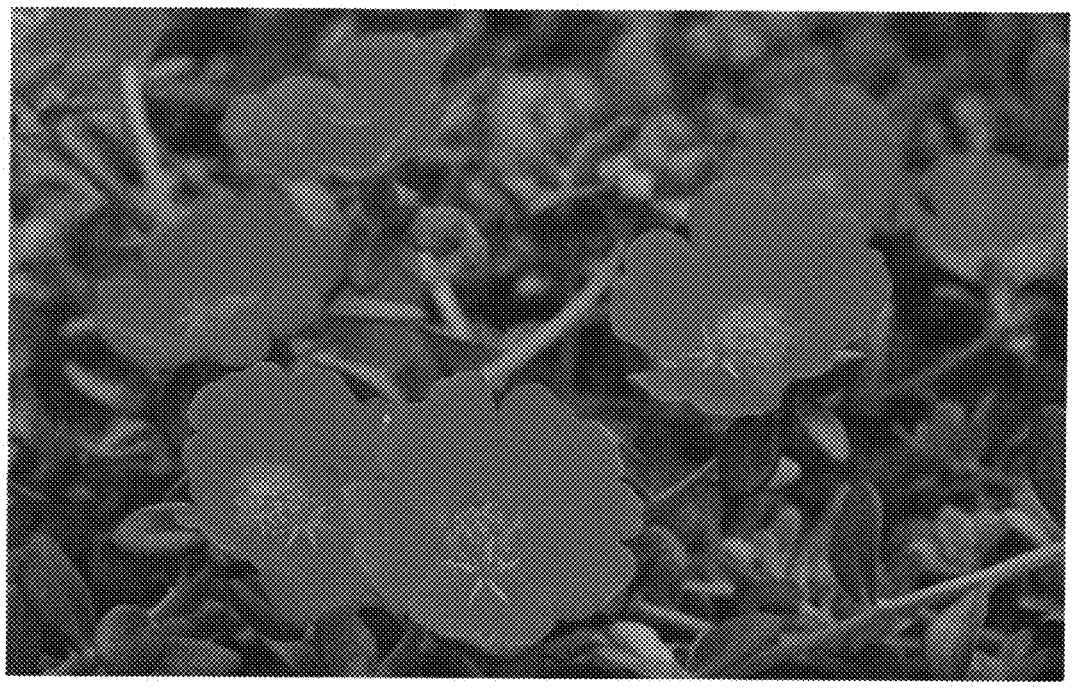

* * * * *